United States Patent
Atzinger et al.

(10) Patent No.: US 9,986,959 B2
(45) Date of Patent: Jun. 5, 2018

(54) ARRANGEMENT FOR PROTECTING CABLES AND LINES IN C-ARMS, AND X-RAY IMAGING APPARATUS

(71) Applicants: Michael Atzinger, Seybothenreuth (DE); Berthold Baumann, Kastl (DE); Franz Fadler, Hetzles (DE); Claus Fleischmann, Bad Vilbel (DE); Stefan Groß, Trabitz (DE); Matthias Hoff, Marktredwitz (DE); Thomas Kleber, Moosbach (DE); Alexander Krämer, Irchenrieth (DE); Harald Mulzer, Speinshart (DE)

(72) Inventors: Michael Atzinger, Seybothenreuth (DE); Berthold Baumann, Kastl (DE); Franz Fadler, Hetzles (DE); Claus Fleischmann, Bad Vilbel (DE); Stefan Groß, Trabitz (DE); Matthias Hoff, Marktredwitz (DE); Thomas Kleber, Moosbach (DE); Alexander Krämer, Irchenrieth (DE); Harald Mulzer, Speinshart (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days. days.

(21) Appl. No.: 15/429,540

(22) Filed: Feb. 10, 2017

(65) Prior Publication Data
US 2017/0231585 A1    Aug. 17, 2017

(30) Foreign Application Priority Data

Feb. 12, 2016    (DE) ........................ 10 2016 202 153

(51) Int. Cl.
*H05G 1/06*    (2006.01)
*A61B 6/00*    (2006.01)
(Continued)

(52) U.S. Cl.
CPC .......... *A61B 6/4441* (2013.01); *A61B 6/4464* (2013.01); *A61B 6/4488* (2013.01);
(Continued)

(58) Field of Classification Search
CPC ....... A61B 6/4488; A61B 6/56; A61B 6/4441; A61B 19/40; A61B 2090/0436;
(Continued)

(56) References Cited

U.S. PATENT DOCUMENTS 4,747,119 A * 5/1988 Heinz .................... A61B 6/105
188/42
5,410,584 A * 4/1995 Schaefer .............. A61B 6/4441
378/196
(Continued)

FOREIGN PATENT DOCUMENTS

CN    102256427 A    11/2011
CN    102421364 A    4/2012
(Continued)

OTHER PUBLICATIONS

German Office Action for related German Application No. 10 2016 202 153.2 dated Nov. 18, 2016, with English Translation.
(Continued)

*Primary Examiner* — Irakli Kiknadze
(74) *Attorney, Agent, or Firm* — Lempia Summerfield Katz LLC

(57) ABSTRACT

A system for protecting cables and lines is provided. The system includes a telescopic C-arm and a cable carrier. The telescopic C-arm includes an outer C-arm, an inner C-arm, an outer carriage, and an inner carriage. The outer C-arm, on an outer surface of the outer C-arm, is arranged in a displaceable manner along the outer carriage. The inner C-arm, on an outer surface of the inner C-arm, is arranged in a fixed or displaceable manner on the inner carriage. The
(Continued)

inner carriage is arranged in a displaceable manner along an inner surface of the outer C-arm. The cable carrier connects the outer carriage and the inner carriage. The cable carrier accommodates the cables and the lines and is configured to move freely between the outer C-arm and the inner C-arm.

16 Claims, 3 Drawing Sheets

(51) Int. Cl.
| | |
|---|---|
| *H01R 35/04* | (2006.01) |
| *F16M 11/10* | (2006.01) |
| *F16M 11/20* | (2006.01) |
| *F16M 13/02* | (2006.01) |
| *H05G 1/02* | (2006.01) |
| *F16G 13/16* | (2006.01) |
| *H02G 11/00* | (2006.01) |

(52) U.S. Cl.
CPC ............ *A61B 6/56* (2013.01); *F16M 11/105* (2013.01); *F16M 11/2014* (2013.01); *F16M 13/027* (2013.01); *H01R 35/04* (2013.01); *H05G 1/02* (2013.01); *F16G 13/16* (2013.01); *F16M 2200/065* (2013.01); *H02G 11/006* (2013.01)

(58) Field of Classification Search
CPC ......... A61B 90/04; A61B 6/035; A61B 6/032; A61B 6/4464; A61B 6/00; A61B 6/102; A61B 6/504; A61B 6/12; A61B 6/481; A61B 6/5247; A61B 2090/364; A61B 6/06; A61B 6/463; A61B 6/487; A61B 6/5235; A61B 6/542; A61B 5/0084; A61B 5/7285; A61B 6/027; A61B 6/541; A61B 8/12; A61B 8/5238; A61B 6/0457; A61B 6/467; A61B 6/4405; A61B 6/4233; A61B 6/548; A61B 6/4014; A61B 6/4452; A61B 6/462; A61B 6/4476; A61B 6/4482; A61B 6/5276; A61B 2017/00889; A61B 6/4458; A61B 6/505; A61B 6/588; A61N 2005/1094; A61N 5/1001; A61N 5/1015; A61N 5/103; A61N 5/1048; A61N 5/10; H05G 1/02; H05G 1/08; A61L 15/26; A61L 15/46; A61L 15/62; A61L 2300/216; A61L 2300/22; A61L 2300/404; A61L 2300/604; A61L 2300/802; Y10T 74/19051; G02C 2202/24; G02C 7/028; G02C 7/04; G02C 7/047; C08L 67/04; G05B 19/19; G05B 2219/43162

USPC ............ 378/4, 15, 195–198; 59/78.1
See application file for complete search history.

(56) References Cited

U.S. PATENT DOCUMENTS

| | | | |
|---|---|---|---|
| 6,428,206 B1 | 8/2002 | Watanabe | |
| 6,431,751 B1* | 8/2002 | Everett | A61B 6/4233 378/193 |
| 6,789,941 B1 | 9/2004 | Grady | |
| 7,635,221 B2* | 12/2009 | Spahn | A61B 6/4233 378/194 |
| 9,801,598 B2* | 10/2017 | Zaiki | A61B 6/4441 |
| 9,851,708 B2* | 12/2017 | Heijman | G05B 19/19 |
| 2007/0228283 A1* | 10/2007 | Graumann | G01T 1/2985 250/363.05 |
| 2008/0147924 A1 | 6/2008 | Lambert et al. | |
| 2009/0147924 A1* | 6/2009 | Gross | A61B 6/4441 378/194 |
| 2009/0154652 A1* | 6/2009 | Yi | A61B 6/4464 378/194 |
| 2010/0094124 A1* | 4/2010 | Schoonenberg | A61B 5/0084 600/424 |
| 2010/0150315 A1* | 6/2010 | Filmer | H01J 35/06 378/136 |
| 2010/0150317 A1* | 6/2010 | Herrmann | A61B 6/4441 378/194 |
| 2012/0085078 A1* | 4/2012 | Rijken | H02G 3/0475 59/78.1 |
| 2012/0106701 A1 | 5/2012 | Meek et al. | |
| 2012/0121071 A1 | 5/2012 | Herrmann et al. | |
| 2012/0275571 A1* | 11/2012 | Neuber | A61B 6/4441 378/194 |
| 2012/0321050 A1* | 12/2012 | Bouvier | A61B 6/4405 378/194 |
| 2013/0182822 A1 | 7/2013 | Sakaguchi et al. | |
| 2015/0320370 A1 | 11/2015 | Bouvier et al. | |
| 2017/0181717 A1 | 6/2017 | Tian et al. | |

FOREIGN PATENT DOCUMENTS

| | | |
|---|---|---|
| CN | 103202701 A | 7/2013 |
| CN | 103784155 A | 5/2014 |
| CN | 103908275 A | 7/2014 |
| CN | 104582577 A | 4/2015 |
| EP | 1389707 A2 | 2/2004 |

OTHER PUBLICATIONS

Chinese Office Action for Chinese Application No. 201710074109.3, dated Feb. 23, 2018, with English translation.

* cited by examiner

ARRANGEMENT FOR PROTECTING CABLES AND LINES IN C-ARMS, AND X-RAY IMAGING APPARATUS

CROSS-REFERENCE TO RELATED APPLICATIONS

This application claims the benefit of DE 102016202153.2 filed on Feb. 12, 2016, which is hereby incorporated by reference in its entirety.

TECHNICAL FIELD

Embodiments relate to an arrangement for protecting cables and lines in a telescopic C-arm system, and to an X-ray imaging apparatus having such an arrangement.

BACKGROUND

C-arm X-ray imaging apparatuses assist an attending physician in diagnosing and treating illness and disease in patients. For supplying power to and cooling the X-ray generator and the X-ray detector, the supply cables and lines/hoses may be routed in, and protected by, corrugated hoses. The corrugated hoses are routed externally (e.g., alongside the C-arm contour). The freedom of movement for hospital staff in the treatment rooms, in which space is usually already at a premium, is thus additionally restricted.

U.S. Pat. No. 6,428,206 B1 describes different telescopic C-arm systems having a plurality of C-arms.

SUMMARY AND DESCRIPTION

The present embodiments may obviate one or more of the drawbacks or limitations in the related art. For example, an arrangement for protecting cables and lines in C-arm systems and an X-ray imaging apparatus that reduce the amount of installation space required are provided.

Externally located corrugated hoses are replaced by a cable carrier between the C-arms of a telescopic C-arm system. Lines and cables may thus be routed in a reliable and defined manner.

The cable carrier (e.g., an energy chain, E-chain, or drag chain) is a mechanical engineering component that routes and protects flexible cables and pneumatic or hydraulic lines. The cables are connected to a machine part that is moved continuously back and forth. Without such a guide that provides that the smallest admissible bending radius of the cables is maintained, the cables, subjected to continuous loading, would be quickly destroyed.

In an embodiment, an arrangement for protecting cables and lines is provided that includes a telescopic C-arm system. The telescopic C-arm system includes an outer C-arm, an inner C-arm, an outer carriage and an inner carriage. The outer C-arm, on an outer side, is arranged in a displaceable manner along the outer carriage. The inner C-arm, along an outer side (e.g., outer surface), is arranged in a fixed or displaceable manner on the inner carriage. The inner carriage is arranged in a displaceable manner along the inner side (e.g., inner surface) of the outer C-arm. The arrangement also includes a cable carrier that connects the outer carriage and the inner carriage. The cable carrier is configured to accommodate cables and lines. The cable carrier is configured to move freely between the outer C-arm and the inner C-arm.

Embodiments provide for eliminating externally located corrugated hoses, which reduces the amount of installation space required, to the benefit of the hospital staff.

In an embodiment, the arrangement includes an X-ray generator and an X-ray detector. The X-ray generator and the X-ray detector are arranged opposite one another on the inner C-arm.

In a further embodiment, the arrangement includes cables for supplying power to the X-ray generator and/or the X-ray detector. The cables are arranged in the interior of the cable carrier.

In a further embodiment, the arrangement includes lines for cooling the X-ray generator and/or the X-ray detector. The lines are arranged in the interior of the cable carrier.

In a further configuration, the arrangement includes a flexible sheathing for the cable carrier. The sheathing is configured to protect the interior of the cable carrier against particles and liquids and to be cleaned straightforwardly.

In an embodiment, the bending radius of a side of the cable carrier that is directed toward the inner C-arm is selected such that the cable carrier does not come into contact with the outer surface of the inner C-arm during operation.

In an embodiment, the cable carrier may be made from plastics material.

In an embodiment, an X-ray imaging apparatus including an arrangement according to one or more of the present embodiments is provided. The arrangement is arranged on the ceiling or on the floor of a room.

The scope of the present invention is defined solely by the appended claims and is not affected to any degree by the statements within this summary.

DETAILED DESCRIPTION

Figure 1:
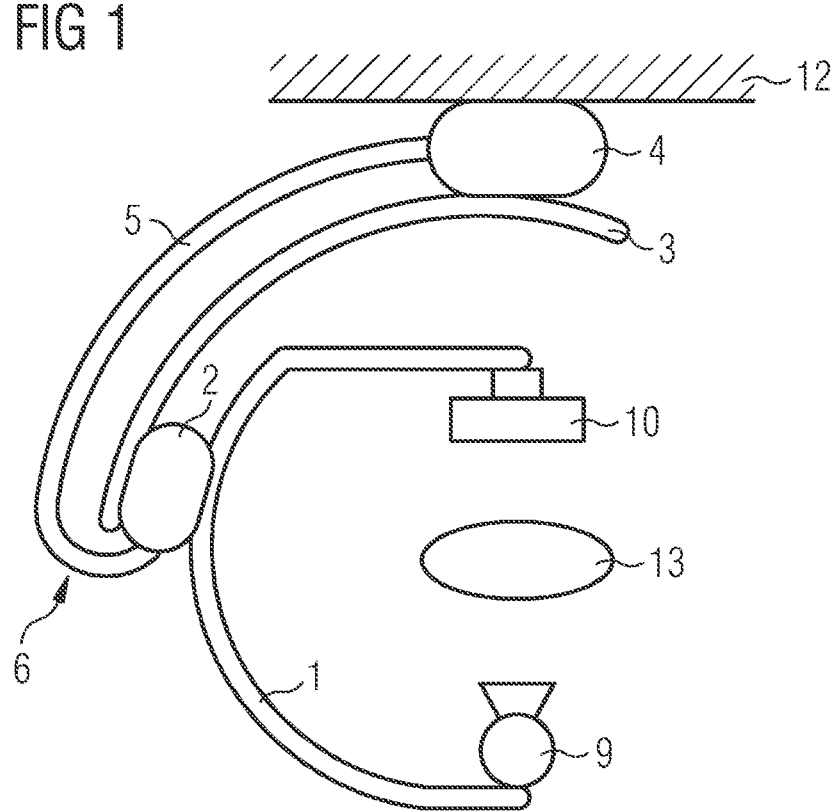
FIG. 1 depicts a side view of a telescopic C-arm system in a 0° position with a cable carrier according to an embodiment.

FIG. 1 depicts a side view of one embodiment of a telescopic C-arm system in a starting position of 0° with a cable carrier 5. The C-arm system includes an inner C-arm 1 (e.g., a first C-arm) and an outer C-arm 3 (e.g., an outer C-arm). The outer C-arm 3 is connected in a displaceable manner to a second carriage 4, and therefore, the outer C-arm 3 may execute an orbital movement. The second carriage 4 is arranged on the ceiling 12 (e.g. room ceiling) of a room (e.g. with a ceiling supported C-arm system).

Between the first C-arm 1 and the second C-arm 3 is a first carriage 2 that may be displaced along the inner side of the second C-arm 3. The first C-arm 1 is connected in a displaceable manner to the first carriage 2 on an outer side. The first C-arm 1 may execute an orbital movement.

An X-ray generator 9 is fastened at one end of the first C-arm 1. Opposite the X-ray generator, an X-ray detector 10 is fastened at the other end of the first C-arm 1. By moving the C-arms 1 and 3 telescopically, the X-ray generator 9 and the X-ray detector 10 may execute an orbital movement of more than 180°. An object 13 for examination (e.g., a patient) is located in the isocenter between the X-ray generator 9 and the X-ray detector 10.

The cable carrier 5 includes one end fastened to the first carriage 2 and the other end fastened to the second carriage 4. The cable carrier 5 therefore executes movements of the carriages 2 and 4 and is guided along the C-arm curvature between the first C-arm 1 and the second C-arm 3.

In order to meet hygiene related requirements of a hospital, the cable carrier 5 includes a flexible sheathing 6 made of plastics material. The sheathing prevents particles of dirt and liquids from penetrating into the cable carrier 5. The sheathing 6 also allows for the cable carrier 5 to be cleaned straightforwardly and hygienically from the outside.

Cables and lines (not visible in FIG. 1) for supplying the X-ray generator 9 and the X-ray detector 10 are incorporated in the interior of the cable carrier 5. The cables and lines are protected against mechanical influences and may execute defined movements with defined bending radii. The minimum bending radius is determined by the structural shape of the cable carrier.

Figure 2:
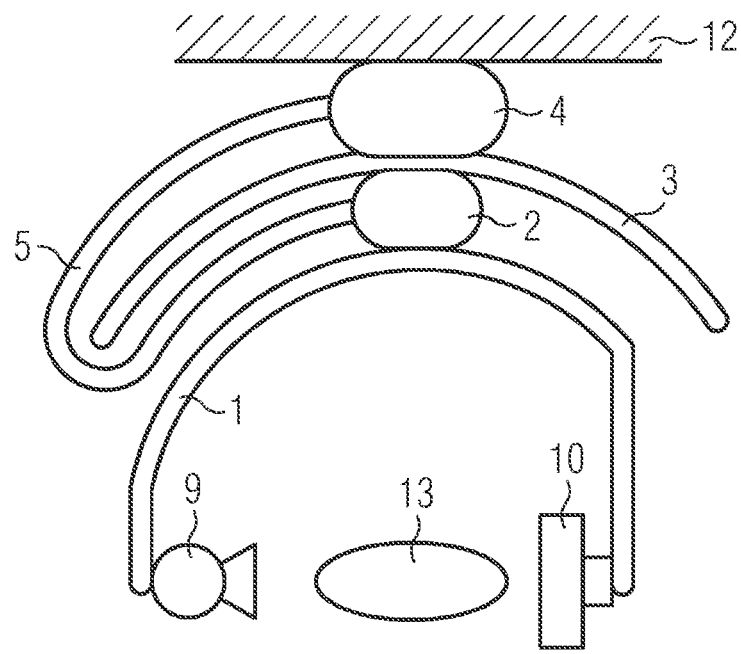
FIG. 2 depicts a side view of a telescopic C-arm system in a 90° position with a cable carrier according to an embodiment.

FIG. 2 depicts a side view of one embodiment of a telescopic C-arm system according to FIG. 1 in an operating position of 90°. In relation to FIG. 1, the first carriage 2 and the second C-arm 3 have moved in the clockwise direction to the extent where the X-ray generator 9 and the X-ray detector 10 have now been rotated through 90° in a clockwise direction about the isocenter. The cable carrier 5 runs between the first C-arm 1 and the second C-arm 3 without coming into contact with the first C-arm 1.

Figure 3:
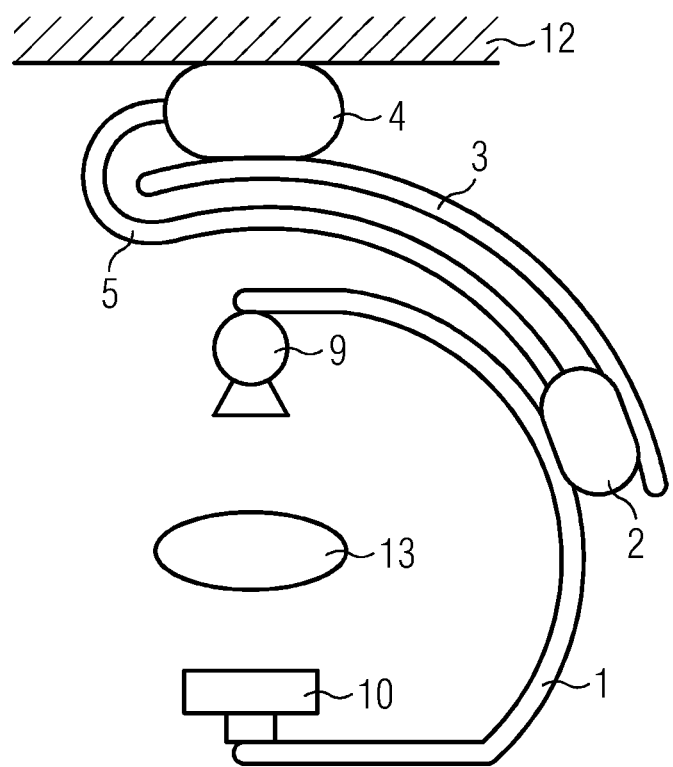
FIG. 3 depicts a side view of a telescopic C-arm system in a 180° position with a cable carrier according to an embodiment.

FIG. 3 depicts a side view of one embodiment of a telescopic C-arm system according to FIG. 1 in an operating position of 180°. In relation to FIG. 1, the first carriage 2, the second C-arm 3, and the first C-arm 1 have moved in a clockwise direction to the extent where the X-ray generator 9 and the X-ray detector 10 have now been rotated through 180° in the clockwise direction about the isocenter. The cable carrier 5 runs between the first C-arm 1 and the second C-arm 3 without coming into contact with the first C-arm 1. In relation to FIG. 2, the C-arm system has been rotated through 90° in the clockwise direction.

In order to avoid the cable carrier 5 striking against the outer surface of the inner C-arm 1 and accompanying problems relating to the development of noise and also friction, the rear-side bending radius (e.g., an inner radius) of the cable carrier 5 is delimited. The cable carrier 5 does not sag, and the cable carrier 5 is routed at a defined distance above the outer surface of the inner C-arm 1.

Figure 4:
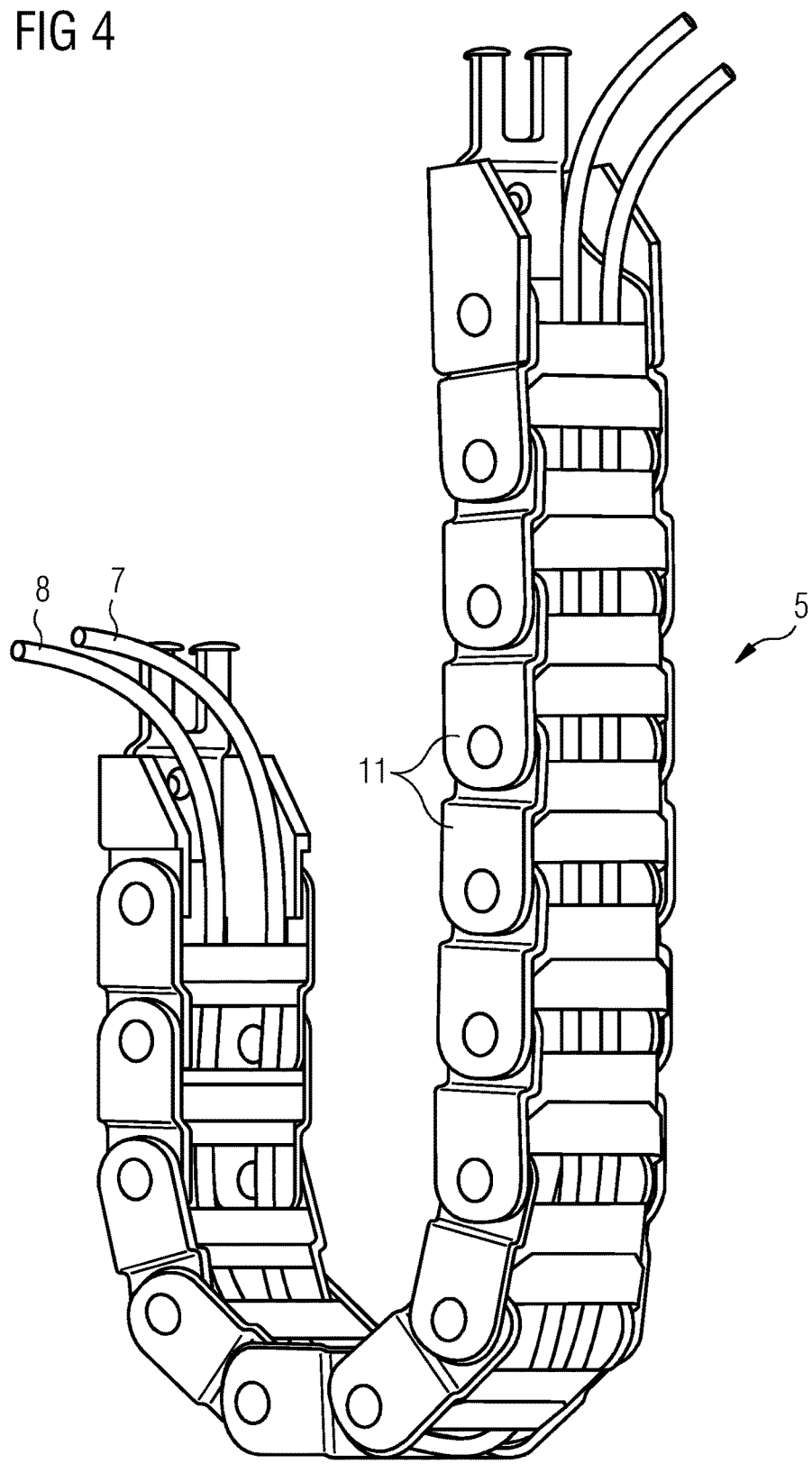
FIG. 4 depicts a three-dimensional view of a cable carrier according to an embodiment.

FIG. 4 depicts a three-dimensional view of one embodiment of a cable carrier 5 that is formed from chain links 11 made of plastics material. Cables 7 for supplying power and lines 8 for feeding a coolant are incorporated in the interior of the chain links 11. For the sake of clarity, only one cable and only one line are depicted in FIG. 4.

In an embodiment, the cable carriers have a rectangular cross section. The cables and the lines are located in the interior of the rectangular cross section. A starting piece and an end piece are connected by a plurality of identical chain links. In an embodiment, the chain links are opened on the outside so that cables, even with a plug connected, may be incorporated therein. Crosspieces in the cable carrier separate the cables and lines from one another. At the start and at the end, the cables and lines are clamped by way of the strain relief.

Cable carriers may be produced from plastics material (e.g. polypropylene or polyamide). In an embodiment, the cable carriers may be made of metal for heavy hydraulic lines or large chains.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A system for protecting a plurality of cables and a plurality of lines, the system comprising:
    a telescopic C-arm system comprising:
        an outer C-arm having a first outer surface and a first inner surface;
        an inner C-arm have a second outer surface and a second inner surface;
        an outer carriage; and
        an inner carriage, wherein the outer C-arm, on the first outer surface, is arranged in a displaceable manner along the outer carriage, wherein the inner C-arm, on the second outer surface, is arranged in a fixed or displaceable manner on the inner carriage, and wherein the inner carriage is arranged in a displaceable manner along the first inner surface of the outer C-arm; and
    a cable carrier that directly connects the outer carriage and the inner carriage and is configured to accommodate the plurality of cables and the plurality of lines, the cable carrier further configured to move freely between the outer C-arm and the inner C-arm.

2. The system of claim 1, further comprising:
    an X-ray generator; and
    an X-ray detector,
    wherein the X-ray generator and the X-ray detector are arranged opposite one another on the inner C-arm.

3. The system of claim 2, wherein the plurality of cables are configured to supply power to the X-ray generator, the X-ray detector, or the X-ray generator and the X-ray detector and are arranged in an interior of the cable carrier.

4. The system of claim 2, wherein the plurality of lines are configured to cool the X-ray generator, the X-ray detector, or the X-ray generator and the X-ray detector and are arranged in an interior of the cable carrier.

5. The system of claim 1, further comprising:
    a flexible sheathing for the cable carrier, the flexible sheathing configured to protect an interior of the cable carrier.

6. The system of claim 1, wherein a bending radius of a first side of the cable carrier that is directed toward the inner C-arm is selected such that the cable carrier does not come into contact with the inner C-arm during operation.

7. The system of claim 1, wherein the cable carrier is formed from plastics material.

8. The system of claim 1, wherein the inner carriage is arranged on a ceiling of a room.

9. An X-ray imaging apparatus comprising:
a system for protecting a plurality of cables and a plurality of lines, the system comprising:
a telescopic C-arm system comprising:
an outer C-arm having a first outer surface and a first inner surface;
an inner C-arm have a second outer surface and a second inner surface;
an outer carriage; and
an inner carriage, wherein the outer C-arm, on the first outer surface, is arranged in a displaceable manner along the outer carriage, wherein the inner C-arm, on the second outer surface, is arranged in a fixed or displaceable manner on the inner carriage, and wherein the inner carriage is arranged in a displaceable manner along the first inner surface of the outer C-arm; and
a cable carrier that directly connects the outer carriage and the inner carriage;
wherein the cable carrier and is configured to accommodate the plurality of cables and the plurality of lines, the cable carrier further configured to move freely between the outer C-arm and the inner C-arm.

10. The X-ray imaging apparatus of claim 9, further comprising:
an X-ray generator; and
an X-ray detector,
wherein the X-ray generator and the X-ray detector are arranged opposite one another on the inner C-arm.

11. The X-ray imaging apparatus of claim 10, wherein the plurality of cables are configured to supply power to the X-ray generator, the X-ray detector, or the X-ray generator and the X-ray detector and are arranged in an interior of the cable carrier.

12. The X-ray imaging apparatus of claim 10, wherein the plurality of lines are configured to cool the X-ray generator, the X-ray detector, or the X-ray generator and the X-ray detector and are arranged in an interior of the cable carrier.

13. The X-ray imaging apparatus of claim 9, wherein the system further comprises:
a flexible sheathing for the cable carrier, the flexible sheathing configured to protect an interior of the cable carrier.

14. The X-ray imaging apparatus of claim 9, wherein a bending radius of a first side of the cable carrier that is directed toward the inner C-arm is selected such that the cable carrier does not come into contact with the inner C-arm during operation.

15. The X-ray imaging apparatus of claim 9, wherein the cable carrier is formed from plastics material.

16. The X-ray imaging apparatus of claim 9, wherein the inner carriage is arranged on a ceiling of a room.

* * * * *